United States Patent [19]

Hara

[11] Patent Number: 4,720,786
[45] Date of Patent: Jan. 19, 1988

[54] METHOD OF COMPENSATING FOR OFFSET DISTORTION IN ROWS OF ELECTROPHORETIC PATTERNS

[75] Inventor: Makoto Hara, Kanagawa, Japan

[73] Assignee: Fuji Photo Film Co., Ltd., Japan

[21] Appl. No.: 854,381

[22] Filed: Apr. 21, 1986

[30] Foreign Application Priority Data

Apr. 19, 1985 [JP] Japan .................. 60-85275
Apr. 19, 1985 [JP] Japan .................. 60-85276

[51] Int. Cl.$^4$ .................. C12Q 1/68; G01N 33/58
[52] U.S. Cl. .................. 364/413; 435/6; 935/77
[58] Field of Search .................. 364/413; 935/77, 78, 935/86, 87; 435/6, 808

[56] References Cited

FOREIGN PATENT DOCUMENTS

| 0113672 | 7/1984 | European Pat. Off. . | |
| 0141382 | 5/1985 | European Pat. Off. . | |
| 0157280 | 10/1985 | European Pat. Off. | 435/6 |
| 1018865 | 1/1986 | Japan | 435/6 |
| WO86/05817 | 10/1986 | PCT Int'l Appl. | 435/6 |

OTHER PUBLICATIONS

Sanger, F. et al. "DNA Sequencing with Chain-Terminating Inhibitors," *Proc. Natl. Acad. Sci.*, vol. 74, No. 12, Dec. 1977, 5463–5467.

Primary Examiner—Jerry Smith
Assistant Examiner—Clark A. Jablon
Attorney, Agent, or Firm—Gerald J. Ferguson, Jr.; Michael P. Hoffman; Michael J. Foycik, Jr.

[57] ABSTRACT

The base sequence of nucleic acids is determined by subjecting digital signals to signal processing, where the digital signals correspond to an autoradiograph of plural resolved rows which are formed by resolving a mixture of base-specific DNA fragments or base-specific RNA fragments labeled with a radioactive element in one-dimensional direction on a support medium.

The method involves detecting at least two bands in the lower part of each resolved row and numbering the bands consecutively from the lower end, obtaining correlation between the band's number and a resolved distance thereof for each resolved row, and then determining the difference in the resolved distance between the resolved rows from the resulting correlation and making correction for the resolved position on each row by taking the difference as a locational deviation of the rows from each other.

25 Claims, 6 Drawing Figures

SLOT POSITION $x$ $y_0$  $y$
SIGNAL POSITION

METHOD OF COMPENSATING FOR OFFSET DISTORTION IN ROWS OF ELECTROPHORETIC PATTERNS

BACKGROUND OF THE INVENTION

1. Field of the Invention

This invention relates to a signal processing method for determining base sequence of nucleic acids.

2. Description of the Prior Art

It is essential to obtain genetic information carried by organisms in order to make the function or replicated mechanism of the organism clear in the field of molecular biology which has been rapidly developed in recent years. Particularly, it is essential to determine base sequence of nucleic acids such as DNA (or DNA fragment; the same applies hereinbelow) which carries specific genetic information.

Maxam-Gilbert method and Sanger-Coulson method are known as typical methods for determining the base sequence of nucleic acids such as DNA and RNA. In the former Maxam-Gilbert method, a group containing a radioactive isotope such as $^{32}P$ is attached to a chain molecule of DNA or a DNA fragment at one end to label it with the radioactive element and then the bond between the constitutional units of the chain molecular is base-specifically cleaved by a chemical reaction. A mixture of the resulting base-specific DNA cleavage products is resolved through gel electrophoresis to obtain a resolved pattern (not visible) wherein each of the numerous cleavage products is resolved on the gel support medium. The resolved pattern is visualized on a radiographic film such as an X-ray film to obtain an autoradiograph thereof as a visible image. The bases in certain positional relationships with the end of the radioactive element-attached chain molecular can be sequentially determined according to the visualized autoradiograph and the applied base-specific cleavage means. In this way, the sequence for all bases of the DNA specimen can be determined.

In the latter Sanger-Coulson method, synthetic DNA products which are complementary to the chain molecule of DNA or DNA fragment and radioactively labeled, are basespecifically synthesized by utilizing a chemical reaction, and the obtained mixture of numerous synthetic DNA products is resolved on a support medium by gel electrophoresis to obtain a resolved pattern. In a similar manner to that described above, the base sequence of DNA can be determined according to the visualized autoradiograph.

For the purpose of carrying out the determination of the base sequence of nucleic acids simply with high accuracy in autoradiography, there are described in U.S. application Ser. No. 549,417, abandoned (now pending as U.S. application Ser. No. 837,037) and U.S. application Ser. No. 902,101, a continuation of abandoned U.S. application No. 664,405 autoradiographic procedures which utilize a radiation image recording and reproducing method using a stimulable phosphor sheet, in place of conventional radiography using a radiosensitive material such as an X-ray film. The stimulable phosphor sheet comprises a stimulable phosphor and has such properties that when exposed to a radiation, the stimulable phosphor absorbs a portion of radiation energy and then emits light (stimulated emission) corresponding to the radiation energy stored therein upon excitation with an electromagnetic wave (stimulating rays) such as visible light or infrared rays. According to this method, exposure time can be greatly shortened and there is no fear of causing problems such as chemical fog associated with prior arts. Further, since the autoradiograph having information on radioactively labeled substances is stored in the phosphor sheet as radiation energy and then read out as stimulated emission in time sequence, information can be expressed by the form of numerals and/or symbols in addition to image.

The base sequence of the nucleic acids has been conventionally determined by visually judging individual resolved positions of the base-specific cleavage products or the base-specific synthetic products of radioactively labeled nucleic acid (hereinafter referred to simply base-specific fragments of nucleic acid) on the autoradiograph and comparing them among the resolved rows thereof. Namely, the analysis of the autoradiogrpah is done by observing the visualized autoradiograph with eyes, and such visual analysis requires great amounts of time and labor.

Further, since the visual analysis of the autoradiograph varies or fluctuates owing to the skill of investigators, the results on the determination of the base sequence of nucleic acid vary depending on the investigators and the accuracy of information is limited to a certain extent.

In order to improve the accuracy of the information, there are proposed in pending U.S. application Nos. 024,909 continued from 865,956 and 568,877, both now abandoned, and U.S. application Ser. No. 730,034 methods for automatically determining the base sequence of DNA by obtaining the autoradiograph as digital signals and subjecting the digital signals to appropriate signal processing. The digital signals corresponding to the autoradiograph of the radioactively labeled substances can be obtained either by visualizing the autoradiograph on a radiographic film and photoelectrically reading out the visible image on said film by means of reflected light or transmitted light when the conventional radiography is employed, or by directly reading out the stimulable phosphor sheet without the visualization of the autoradiograph when the radiation image recording and reproducing method is employed.

However, the resolved pattern obtained by resolving (developing) radioactively labeled substances on a support medium by electrophoresis or the like is liable to cause various distortion and noise. A typical example thereof is offset distortion, that is, the deviation (slippage) of the position of the overall rows from one another due to differing resolution starting position or starting time among the rows. The offset distortion is caused mainly by that the shapes (the size of recess) of many slots (sample introducing ports) provided in the upper part of a support medium such as a gel medium are not always identical and there is a difference between individuals. There also bring about the offset distortion that positions on which the sample is to be deposited are deviated from one another in introducing the sample into the support medium and that the penetration rates of the sample into the support medium are different from one another when the washing of urea out of the gel medium is insufficient just before the introduction of the sample.

FIG. 1 shows an example where a resolved pattern causes offset distortion due to unevenness in the shapes of slots. FIG. 1-(a) shows the upper part of a support medium which has been used for the resolution of a sample and FIG. 1-(b) shows a resolved pattern obtained by introducing the same sample into each of slots (1) to (4) and then resolving it. The recess of the third slot is deeper than those of other slots as shown in FIG. 1-(a), and hence, the resolved row of the third slot is slipped downward as a whole and locational deviation ($\Delta y$) thereof from other slots is produced as shown in FIG. 1-(b). Such relative locational deviation of the rows from each other is called offset distortion.

It is highly demanded to automatically determine the base sequence of the nucleic acids with high accuracy by subjecting digital signals corresponding to the autoradiograph to efficient signal processing, even when such distortion is caused.

SUMMARY OF THE INVENTION

The present inventor has found that the base sequence of the nucelic acids can be automatically determined with easiness and high accuracy by suitably processing the digital signals corresponding to the autoradiograph in the method for the automatic determination of the base sequence using autoradiography, even when the resolved pattern causes the offset distortion.

The present invention provides a signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in one-dimensional direction on a support medium,
which comprises steps of:
(1) detecting at least two bands in the lower part of each resolved row and numbering the bands consecutively from the lower end;
(2) obtaining correlation between the band's number and a resolved distance thereof for each resolved row; and
(3) determining difference in the resolved distance between the resolved rows from the resulting correlation and making correction for resolved position on each row by taking said difference as locational deviation of the rows from each other.

The present invention also provides a signal processing method for determining the base sequence of nucleic acids by subjecting said digital signals corresponding to an autoradiograph to signal processing, which comprises steps of:
(1) detecting at least two bands in the lower part of each resolved row and numbering the bands consecutively from the lower end;
(2) obtaining correlation between the band's number and a resolved distance thereof for each resolved row;
(3) determining difference in the resolved distance between the resolved rows from the resulting correlation and making correction for resolved position on each row by taking said difference as locational deviation of the rows from each other; and
(4) detecting all bands on every resolved row and determining the sequence of the bands on the basis of their positions.

The present invention further provides a signal processing method for determining the base sequence of nucleic acids by subjecting said digital signals corresponding to an autoradiograph to signal processing, which comprises steps of:

(1) detecting at least two bands in the lower part of each resolved row and numbering the bands consecutively from the lower end;
(2) obtaining correclattion between the band's number and a resolved distance thereof for each resolved row;
(3) determining difference in the resolved distance between the resolved rows from the resulting correlation;
(4) detecting at least one band in the more upper part of each resolved row, making correction for resolved position on each band by taking the resulting difference as locational deviation of the rows from each other, and then numbering the bands consecutively on the basis of their positions;
(5) obtaining the correlation between the band's number and the resolved distance with respect to the previously detected bands plus the band detected in the step (4) for each resolved row; and
(6) determining the sequence of all bands on every resolved row the basis of their corrected positions by repeating the steps (3) to (5).

According to the present invention, the base sequence of the nucleic acids can be simply determined with high accuracy by processing digital signals corresponding to the autoradiograph of the resolved pattern of a mixture of base-specific fragments of a nucleic acid resolved on a support medium through a suitable signal processing circuit having a function capable of making the correction for offset distortion even when the resolved pattern causes the offset distortion.

Generally, the resolved pattern has such a band distribution that spaces among resolved bands are sparse in the lower part (region where resolved distance is long) of the pattern and become denser toward the resolution starting position in the upper part thereof. The term "lower part" means a region below nearly the middle of the support medium and the term "upper part" means a region above it. Accordingly, even when the offset distortion is caused among the resolved rows and the positions of bands are overall deviated from those of other rows, the sequence of the bands in the lower part can be easily determined by comparing the band positions on each row with each other. However, there is much difficulty in determining the sequence of bands in the upper part since the band spaces are dense in the upper region, to cause an error in the determination of the base sequence of the nucleic acids.

The present inventor paid attention to the fact that there is a difference in the band spaces between the upper part and the lower part of the resolved pattern and that the sequence of the bands can be easily determined in the lower part even when the offset distortion is caused. As a result, the inventor has accomplished a method for making properly and simply the correction for the offset distortion.

More in detail, the band sequence can be easily determined in the lower region and there is a certain correlation between the consecutive band's number and the resolved distance thereof for each row. Usually, the correlation therebetween is nearly linear so that the correlation canbe approximated by a straight line. Accordingly, in the first aspect of the present invention (the first and second methods), the deviation of the band position of the rows from each other can be simply determined and the correction for the offset distortion can be made en bloc.

Further, in the second aspect of the invention (the third method), the deviation of the band position of the rows can be partially determined in the lower region and the correction for the offset distortion can be made successively, when the correlation between the band's number and the resolved distance thereof is not linear. Especially, the correlation therebetween can be locally approximated by a straight line and easily obtained when the bands employed therefor are not so many. The third method of the invention is a method of making correction successively for the location deviation of the rows, and the correction for position can be made with high accuracy even when the degree of the location deviation varies locally in the direction of resolution.

Thus, the base sequence of the nucleic acids can be easily determined with high accuracy by subjecting the offset distortion-corrected digital signals to further suitable signal processing.

DETAILED DESCRIPTION OF THE INVENTION

Figure 1:
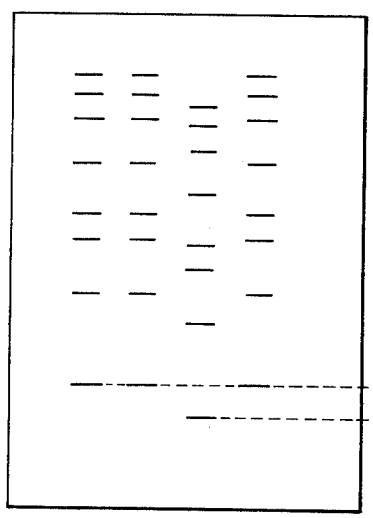
FIG. 1-(a) is a partial view showing the shapes of slots provided in the upper part of a support medium, and FIG. 1-(b) shows an example of a resolved pattern which causes offset distortion.

Examples of samples employable in the present invention include mixtures of base-specific fragments of nucleic acids such as DNA and RNA labeled with a radioactive element. The term "fragments" of nucleic acids mean portions of a long-chain molecule. For instance, a mixture of base-specific DNA cleavage products, which is a kind of a mixture of base-specific DNA fragments, can be obtained by base-specifically cleaving the radioactively labeled DNA according to the aforementioned Maxam-Gilbert method. A mixture of base-specific DNA synthetic products can be obtained by synthesizing from radioactively labeled deoxynucleoside triphosphates and DNA polymerase by use of DNA as a template according to the aforementioned Sanger-Coulson method.

Mixtures of base-specific RNA fragments can be also obtained as a mixture of cleavage products or a mixture of synthetic products in the similar manner to the above-described methods. DNA is composed of four kinds of bases: adenine, guanine, thymine and cytosine as its constitutional units, and RNA is composed of four kinds of bases: adenine, guanine, uracil and cytosine.

These substances can be labeled with a radioactive element such as $^{32}P$, $^{14}C$, $^{36}S$, $^{3}H$ or $^{125}I$ by any of appropriate methods.

A sample, which is a mixture of the base-specific fragments of a nucleic acid labeled with a radioactive element, can be resolved (developed) on a known support medium such as a gel support medium by any of conventional resolving (developing) procedures such as electrophoresis, thin layer chromatography, column chromatography and paper chromatography.

The support medium on which the radioactively labeled substances are resolved, is autoradiographed to obtain an autoradiograph thereof by means of the conventional radiography using a radiosensitive material or the radiation image recording and reproducing method using a stimulable phosphor sheet. The digital signals corresponding to the autoradiograph can be then obtained through an appropriate read-out system.

When the conventional radiography is used, the support medium and a radiosensitive material such as a X-ray film are placed together in layers at a low temperature of $-90°$ to $-70°$ C. for a long period of time (several tens of hours) to expose the radiographic film. The radiographic film is then developed to visualize the autoradiograph of the radioactively labeled substances on the film, and the visualized autoradiograph is read out by using an image read-out system. For instance, the radiographic film is irradiated with a light beam and the light transmitted thereby or reflected therefrom is photoelectrically detected, whereby the autoradiograph can be obtained as electric signals. Further, digital signals corresponding the electric signals are obtained through A/D conversion.

When the radiation image recording and reproducing method is used, the support medium and the stimulable phosphor sheet are placed together in layers at an ambient temperature for a short period of time (several seconds to several tens of minutes) to store radiation energy radiating from the radioactively labeled substances in the phosphor sheet, whereby the autoradiograph is recorded as a kind of a latent image (energy-stored image) on the phosphor sheet. The stimulable phosphor sheet has a basic structure where a support comprising, for instance, a plastic film, a phosphor layer comprising a stimulable phosphor such as a divalent europium activated barium fluorobromide phosphor ($BaFBr:Eu^{2+}$) and a transparent protective film are laminated in this order. The stimulable phosphor contained in the stimulable phosphor sheet has such characteristics that the phorphor absorbs and stores radiation energy emitted by the labeled substances when irradiated with a radiation such as X-rays and then releases the stored radiation energy as stimulated emission when excited with visible light to infrared rays.

Subsequently, the autoradiograph stored and recorded on the stimulable phosphor sheet is read out by using a read-out system. For instance, the phosphor sheet is scanned with a laser beam to release the radiation energy stored in the stimulable phosphor as light emission and the emitted light is photoelectrically detected, so that the autoradiograph can be directly obtained as electric signals without the visualization of the autoradiograph. Further, digital signals corresponding to the autoradiograph can be obtained from the electric signals through A/D conversion.

The above-described methods for measuring the autoradiograph and obtaining the digital signals corresponding thereto are described in more detailed in the aforementioned U.S. application Ser. No. 549,417, abandoned (now pending as U.S. application Ser. No. 837,937) Ser. and pending U.S. application Ser. Nos. 024,909 continued from 865,956 and 568,877, both now abandoned.

While the methods for obtaining the digital signals corresponding to the autoradiograph using the conventional radiography and the radiation image recording and reproducing method are described above, the present invention is not limited thereto and digital signals obtained by any other methods can be applied to the signal processing method of the invention, provided that they corresponding to the autoradiograph.

In the above read-out procedures, it is not always necessary to conduct the read-out operation of the autoradiograph all over the surface of the radiographic film or the stimulable phosphor sheet. Only the image region may be subjected to the read-out operation.

In the present invention, there may be previously inputted information on the location of each resolved row and the width of band to preset read-out conditions and then conducted scanning at a scanning line density such that each band is traversed by at least two scanning lines in the read-out operation, so as to shorten read-out time and obtain efficiently necessary information. The digital signals corresponding to the autoradiograph in the invention also include the thus-obtained digital signals.

The obtained digital signals $D_{xy}$ comprise a coordinate (x,y) which is represented by a coordinate system defined by the radiographic film or the stimulable phosphor sheet and a signal level (z) at the coordinate. The signal level represents the density of image at the coordinate, that is, the amount of the radioactively labeled substances. Accordingly, a series of the digital signals (that is, digital image data) have information on two-dimensional location of the labeled substances.

The thus-obtained digital signals corresponding to the autoradiograph of the radioactively labeled substances resolved on a support medium, is subjected to signal processing to determine the base sequence of nucleic acid according to the invention described in more detail below.

Now, the signal processing method of the present invention will be described with respect to the first and second method by referring to an example of electrophoretic rows (resolved rows) formed with a combination of the following four groups of base-specific DNA fragments labeled with a radioactive element:

(1) guanine (G)—specific DNA fragments,
(2) adenine (A)—specific DNA fragments,
(3) thymine (T)—specific DNA fragments,
(4) cytosine (C)—specific DNA fragments.

Each of said base-specific DNA fragments is composed of base-specific cleavage products or synthetic products which have various lengths and the same base at terminals.

Figure 2:
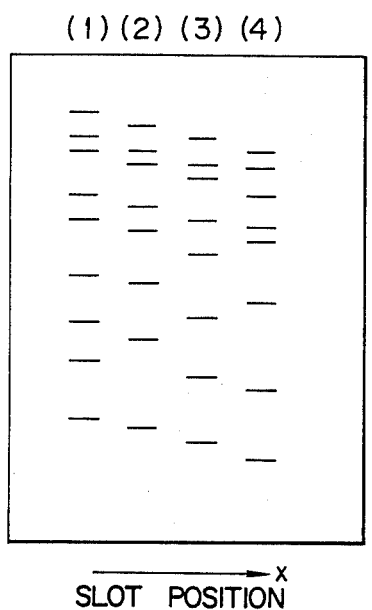
FIG. 2 shows an example of an electrophoretic pattern which causes offset distortion.

FIG. 2 shows the autoradiograph of an electrophoretic pattern obtained by electrophoresing the above four groups of the base-specific DNA fragments in four slots, respectively. The autoradiograph cases offset distortion as shown in FIG. 2.

In the signal processing method of the invention, the digital signals are stored temporarily in a memory device of the signal processing circuit (that is, stored in a non-volatile memory unit such as a buffer memory, a magnetic disk, etc.).

In the first place, at least two bands for each electrophoretic row (lane) are detected and the sequence thereof is determined.

For instance, digital signals within a given zone along the electrophoretic direction of each lane are extracted and a one-dimensional waveform composed of position (y) of the extracted signal and signal level (z) at its position is prepared for each lane. The one-dimensional waveform can be directly prepared, when the detection of the digital signals are carried out by scanning with the laser beam in the electrophoretic direction at such a scanning line density that each band is traversed by a scanning line as described above.

Figure 3:
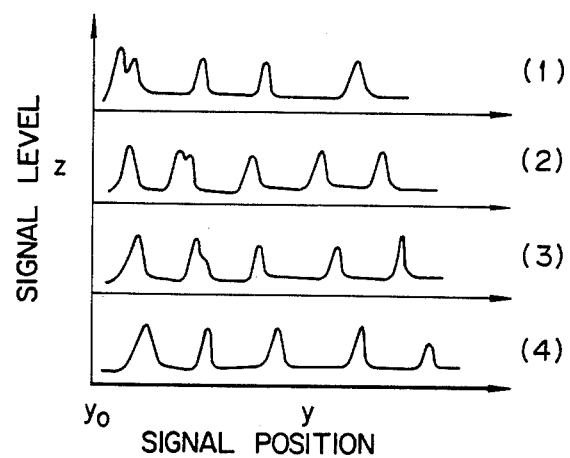
FIG. 3 shows one-dimensional waveforms composed of signal position (y) and signal level (z) for every lane.

FIG. 3 shows one-dimensional waveforms of the individual lanes, which are composed of position (y) of the signals and signal level (z) at its position. In FIG. 3, the position ($y = y_0$) on the ordinate means the base point on the digital image data.

Positions where the signal level is maximum are found out to be defined as the positions of bands, for instance, by searching points where the sign of a difference in signal level is inverted [that is, the sign of the difference is changed from plus(+) to minus(−)] in the right-side region (where y is large) of each one-dimensional waveform of FIG. 3. The number of bands to be detected varies depending on the total number of the bands on the electrophoretic pattern and the pattern profile, and it is preferred to detect about 10 bands per lane when the total number of the bands is in the range of from 150 to 200.

All bands detected are numbered with (n) consecutively in such an order that the band whose electrophoretic position (y) is the farthest from the base point has the lowest number. Since the spaces among the bands are sparse in the lower region of the electrophoretic pattern as evident from the one-dimensional waveforms of FIG. 3, the sequence of the lower band scan be easily determined without causing the inversion of the bands between the lanes, even when the offset distortion is caused.

In the second place, the correlation between the band's number and the migration distance of the band for each lane is determined.

Figure 4:
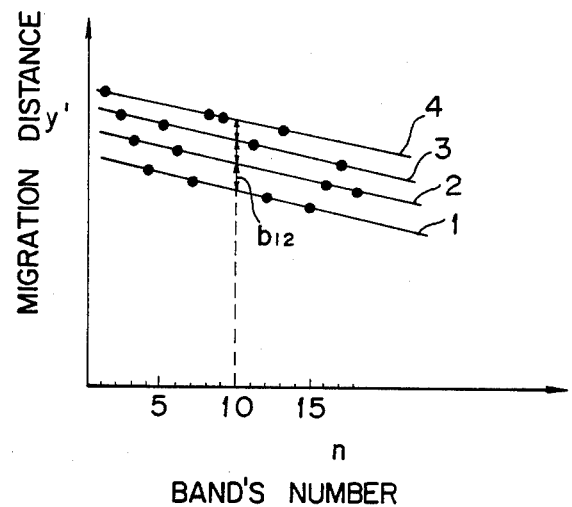
FIG. 4 shows regression lines composed of band's number (n) and migration distance (y') for every lane, wherein the line 1 to 4 correspond to slots (1) to (4), respectively.

For instance, a graph wherein the abscissa represents the band's number (n) and the ordinate represents the migration distance (y') is prepared to obtain a regression line (straight line). FIG. 4 shows regression lines, each consisting of the band's number (n) and the migration distance (y'), wherein each of the lines 1 to 4 corresponds to the slot number.

The migration distance (y') means a distance from the base point ($y_0$) to each band position ($y' = y - y_0$). The base point may be allowed to be the position of the slot. Thus, when there is the locational deviation of the lanes, the distance y' from the common base point is not always the true migration distance. Further, the regression line for each lane can be represented by the following formula:

$$y' = an + b$$

wherein a and b are constants and b is an intercept of y'.

Usually, the relationship between the band's number and the migration distance is locally linear in the lower region of the electrophoretic pattern and is approximated by such a regression line as shown in FIG. 4. Accordingly, the detected bands would exist on one regression line, if no offset distortion were caused. On the other words, four regression lines obtained for all lanes would be superposed with one another into one line.

The correlation between the band's number and the migration distance is by no means limited to be represented by the above-mentioned regression line and other representation mode may be employed. For instance, an appropriate curve of higher-order may be used to approximate the correlation therebetween to obtain a regression curve, thus determining the correlation with high accuracy.

In the third place, the difference(s) in the migration distance between the lanes is determined on the basis of the correlation on each lane and the correction for the migration position on each lane is made on the basis of the difference(s).

In FIG. 4, differences in the migration distance between the lanes are shown as differences in an intercept of the migration distance y' which is measured at an appropriate point on the abscissa. For instance, the difference in the migration distance between the first slot and the second slot is $b_{12}$. This difference in the y' intercept corresponds to the deviation of the band position between the two lanes causes by the offset distoration When the inclinations (a value in the forementioned formula) of the regression lines are different from each other, a difference in y' at a suitable point on the abscissa or the mean value of differences at any points on the abscissa may be taken as the difference in the migration distance. Further, when the correlation is represented by a regression curve, the difference in the migration distance, that is the deviation of the band positions of the lanes, can also be determined in the similar manner.

The positions (y) of the signals on each lane are shifted upward or downward on the basis of the resulting difference in the migration distance. For instance, with regard to the lane of the second slot, the whole of the one-dimensional waveform (2) shown in FIG. 4 is shifted in the direction of the base point on the y-axis by the distance of $b_{12}$ (deduction of the value $b_{12}$ from y), thus making the correction for the migration position all together. In this way, the deviation of the band positions among the lanes can be corrected once for each lane, thus making the correction for the offset distortion of the electrophoretic pattern.

Then (in the fourth place), all positions where signal level is maximum on the migration position-corrected one-dimensional waveform of each lane are found out, whereby all band positions on every lane can be detected.

All the bands are sequenced in order by starting from the lower end of the electrophoretic pattern on the basis of the detected band positions. The sequence can be easily determined on the basis of the fact that two or more bands can not be detected at the same position among the lanes, since a combination of the above four groups of the base-specific DNA fragments is exclusive from each other. The four slots (1) to (4) have information on the terminal base of (G), (A), (T) or (C), respectively, so that the introduction of a base corresponding to the slot to which each band belongs into the band sequence gives the base sequence of DNA. For instance, the base sequence of DNA can be obtained as:

A - G - C - T - A - A - G - . . .

When the electrophoretic pattern causes a smiling phenomenon, correction for the smiling phenomenon may be made before digital signals are subjected to the signal processing for the correction for the offset distortion.

The smiling phenomenon is a phenomenon in which the migration distance of the radioactively labeled substances at the both sides of the support medium are shorter than that in the vicinity of the center thereof. The smiling phenomenon is caused by heat dissipation effect (so-called edge effect), etc. during the electrophoresis.

The smiling phenomenon can be corrected in the following manner.

In the electrophoretic pattern which causes the smiling phenomenon, bands (resolved portion in the shape of rectangle extending perpendicularly to the electrophoretic direction) on lanes at the both sides having a shorter migration distance, is not strictly perpendicular (horizontal) to the electrophoretic direction but inclined according to the degree of the smiling effect. Therefore, the inclination of at least one band for each lane is detected. For instance, the inclination can be determined from a regression line, which is obtained by scanning the digital image data at such a scanning line density that each band is traversed by at least two scanning lines to extract digital signals, preparing a one-dimensional waveform for each scanning line, and then joining positions where signal level is maximum to one another. Alternatively, the digital signals to be extracted may be directly detected in the course of the read-out operation of the autoradiograph.

Subsequently, a band (standard band) on a lane (which is allowed to be a standard lane) which exhibits the smallest smiling effect is extrapolated on each lane other than the standard lane on the basis of the inclination thereof and the inclination of the nearest band on said each lane, to determine the relative position of the standard band on each lane. The ratio of the migration distance for each lane is determined from the position of the standard band and the relative position thereof. The resulting ratio means the degree of the smiling effect of each lane against the standard lane. The migration distance on each lane is extended or shortened in the lump on the basis of said ratio. In this way, the smiling effect can be corrected for all lanes.

Alternatively, the correction for the migration distance can be individually made from band to band by detecting the inclinations of all bands and extrapolating each band on lanes other than the standard lane, to the standard lane on the basis of its inclination.

The methods for the smiling correction are described in more detail in our co-pending Japanese Patent Applications No. 60(1985)-74899 and No. 60(1985)-75900.

The signal processing method of the present invention will be now described with respect to the third method by referring to the above-mentioned example.

Firstly, at least two bands for each lane are detected, the sequence thereof is determined and then the correlation between the band's number and the migration distance of the band such as a regression line or a regression curve is obtained for each lane, in the same manner as described above.

Figure 5:
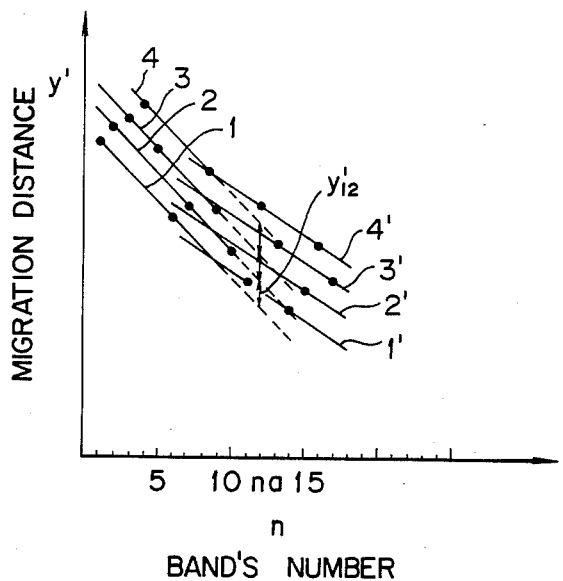
FIG. 5 shows regression lines composed of band's number (n) and migration distance (y') for every lane, wherein the lines 1 to 4 and the lines 1' to 4' correspond to slots (1) to (4), respectively.

FIG. 5 shows regression lines, each consisting of the band's number (n) and the migration distance (y'), wherein each of the lines 1 to 4 corresponds to the slot number.

Secondly, the difference(s) in the migration distance between the lanes is determined from the resulting correlation for the lanes, which is defined as the locational deviation of the lanes from each other in the region of bands to be detected in next.

For instance, the regression lines representing the correlation for the lanes are extrapolated in the direction of increasing n and the migration distances y' at an appropriate point on the abscissa are measured. The differences between these y' are the differences in the migration distance between the lanes in the vicinity at said distances (namely, in the region of bands to be next detected). As shown in FIG. 5, the difference in the migration distance between the lanes of the first and second slots is obtained as a difference $y'_{12}$ at the suitable point ($n=n_a$) by extending the lines 1 and 2 toward the right side (in the direction of increasing n). This difference is the locational deviation of the lane of the second slot from the lane of the first slot caused by the offset distortion.

Thirdly, at least one band is detected in the region more upper than the region where the bands have been already detected. On the newly detected band(s) the correction for the migration position is made on the basis of the obtained locational deviation and the newly detected band(s) are sequenced.

The detection of band is done by finding out the maximum level point on the one-dimensional waveform of each lane in the above-described manner. The correction for the migration position is done by shifting the position (y) of the newly detectecd band(s) upward or downward. For instance, with regard to the band(s) of the second slot, the value $y'_{12}$ is deducted from y to make the correction. In this way, the deviation of the band position of the lanes from each other can be corrected for each lane, thus making the correction for the offset distortion of the electrophoretic pattern.

On the basis of the corrected position of the band(s), the band(s) is compared with each other and numbered consecutively to the fixed number from the lower end. The sequence of the band(s) is easily determined based on the fact of the exclusive combination of the base-specific DNA fragments.

Fourthly, the newly detected band(s) is added to the already detected bands of each lane and in stead of this addition of the band(s), band(s) having the lower number among the already detected bands is excluded therefrom. With regard to these obtained bands, the correlation between the band's number and the migration distance (namely, a regression line or a regression curve) is determined again. As shown in FIG. 5, the new regression lines (lines 1' to 4') are obtained. Since the amount of the data on the bands employed for determining the correlation always keeps constant, the correlation is not noticeably varied depending on the data, but can be represented by the similar formula such as a straight line.

Then, the locational deviation of the lanes in the region of bands to be detected in next is again determined from the modified regression lines, the correction for the migration position is made on further newly detected bands and subsequently, the bands are sequenced.

Thus, the pattern is divided into several zones and the above-described procedure is repeated for each zone to make the correction for the locational deviation caused by the offset distortion on all bands on every lane. Since the locational deviation of the lanes is not always the same over the whole lane, this divisional correction for the locational deviation can achieve the more precise correction for the offset distortion.

The number of bands to be detected and made the correction once is preferably not more than half of the bands employed for obtaining the correlation, and for example, the number thereof is 3 to 5 per lane.

Alternatively, the correlation between the band's number and the migration distance is obtained with respect to all bands detected which consist of the previously detected bands and the newly detected bands. In this case, as the procedure for the divisional correction is repeated, the correlation becomes to be represented not by a straight line but a regression curve obtained by approximating with an appropriate curve (e.g., function of higher-order or exponential function) by means of a method of least squares as shown in FIG. 6.

Figure 6:
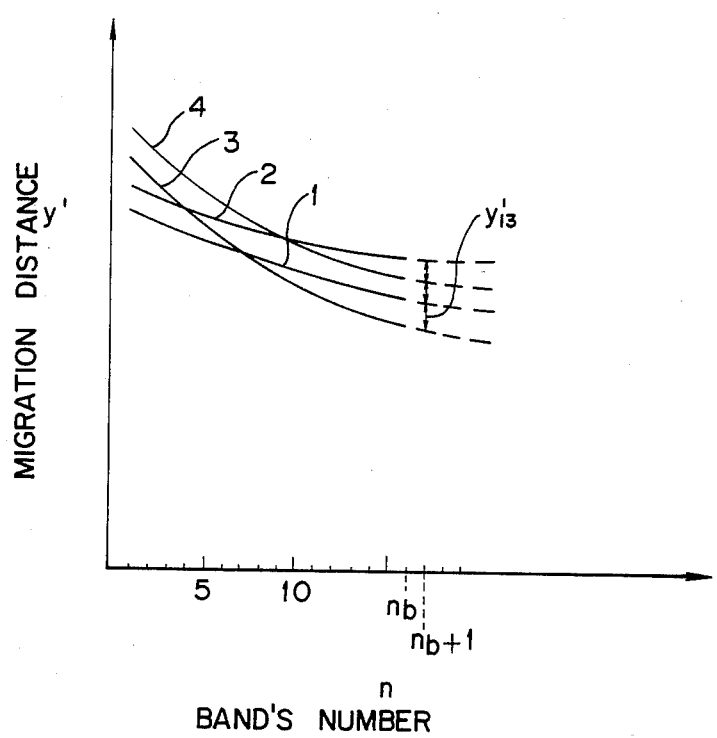
FIG. 6 shows regression curves composed of band's number (n) and migration distance (y') for every lane, wherein the curves 1 to 4 correspond to slots (1) to (4), respectively.

FIG. 6 shows an example of regression curves composed of the band's numer (n) and the migration distance (y') with respect to all detected bands on each lane.

The above-described procedure may be repeated for every band, that is, every time only a band is detected, the correlation between the band's number and the migration distance is modified and then the locational deviation of the lanes in the next band zone is determined. These repeated procedures can bring about the more precise correction for the migration position. For example, as shown in FIG. 6, the regression curves 1 to 4 are determined for the individual lanes based on the data of the 1st to $n_b$-th bands and then extrapolated in the direction of increasing n, whereby the difference in the migration distance between the lane of the first slot and the lane of the third slot is determined at $y'_{13}$ for the $n_b+1$-th band.

Thus, the series of the obtained band's number means the base sequence of DNA. The DNA sequence is obtained by substituting the band sequence respectively with bases corresponding to the slots to which the individual bands belong.

Before the correction for the offset distortion, the correction for the smiling phenomenon can be made also in the third method.

In these ways, the base sequence of one chain molecule of DNA can be determined. The representation mode of the information on the base sequence of DNA is by no means limited to the above-mentioned mode, and other representation modes may be utilized optionally. For instance, the intensity (z') of each band can be represented as the relative amount of the radioactively labeled substances, if desired. Further, the base sequence of both two chain molecules of DNA can be also represented.

Information can be also displayed as an image on the basis of the above-described offset distortion-corrected (and further smiling-corrected) digital signals. At the same time, the original autoradiograph can be displayed as a visualized image. In this case, investigators themselves can finally determine the base sequence on the basis of the display image.

In the above-mentioned example, these has been described the case where the exclusive commbination of the mixture (G, A, T, C) of the base-specific DNA fragments as a sample is used, but the signal processing method of the present invention is by not means limited to the above combination, and other combinations can be used. For instance, a combination of (G, G+A, T+C, C) can be used. Further, the signal processing method of the present invention can be also applied to the mixtures (for instance, a combination of G, A, U, C) of base-specific RNA fragments. Moreover, the correction for the offset distortion is not limited to one set of resolved rows of base-specific fragments of a nucleic acid, but can be made on all resolved rows simultaneously resolved on a support medium.

It is possible to perform the genetic philological information processing such as comparison between the obtained base sequence of the DNA and the base sequence of another DNA which has been already recorded and stored in a suitable means.

The information on the base sequence of DNA determined through the above-described signal processing is output from the signal processing circuit, and subsequently transmitted to a recording device directly or optionally via storage in a storing means such as a magnetic disk or a magnetic tape.

Various recording devices based on various systems can be employed for the above-described purpose, for instance, a device for visualizing optically by scanning a photosensitive material with laser beam, etc., a display means for visualizing electrically on CRT, etc., a means for printing a radiation image displayed on CRT by means of a video printer, and a means for visualizing on a heatsensitive recording material using thermic rays.

I claim:

1. A signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in one-dimensional direction on a support medium, which comprises steps of:
   (1) detecting at least two bands in the lower part of each resolved row and numbering the bands consecutively from the lower end;
   (2) obtaining correlation between the the band's number and a resolved distance thereof for each resolved row; and
   (3) determining difference in the resolved distance between the resolved rows from the resulting correlation and making correction for resolved position on each row by taking said difference as locational deviation of the rows from each other.

2. The signal processing method as claimed in claim 1, wherein said bands are detected by extracting digital signals along the resolving direction of each resolved row and then finding out positions where level of the extracted signal is maximum, in said step (1).

3. The signal processing method as claimed in claim 1, wherein said correlation between the band's number and the resolved distance thereof is obtained as a regression line or a regression curve, in said step (2).

4. The signal processing method as claimed in claim 3, wherein said difference in the resolved distance between the resolved rows is determined as a difference in an intercept of the regression line or the regression curve, in said step (3).

5. The signal processing method as claimed in claim 1, wherein correction for the resolved distance is made on each resolved row by detecting inclination of at least one band to the resolving direction for each row and then determining a relative position of said band on other rows on the basis of the inclination thereof, prior to said step (1).

6. The signal processing method as claimed in claim 1, wherein the mixture of the base-specific DNA fragments consists of the four groups of:
   (1) guanine-specific DNA fragments;
   (2) adenine-specific DNA fragments;
   (3) thymine-specific DNA fragments; and
   (4) cytosine-specific DNA fragments;
and the resolved rows consist of four rows formed by resolving each of said four groups of the base-specific DNA fragments on the support medium.

7. The signal processing method as claimed in claim 1, wherein said digital signals corresponding to the autoradiograph are obtained by placing the support medium and a stimulable phosphor sheet comprising a stimulable phosphor together in layers to record the autoradiograph of the plural resolved rows on the phosphor sheet as an energy-stored image, irradiating said phosphor sheet with stimulating rays and photoelectrically detecting the autoradiograph as stimulated emission.

8. The signal processing method as claimed in claim 1, wherein said digital signals corresponding to the autoradiograph are obtained by placing the support medium and a radiosensitive material together in layers to record the autoradiograph of the plural resolved rows on the radiosensitive material as a visible image and photoelectrically reading out the autoradiograph visualized on said radiosensitive material.

9. A signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in one-dimensional direction on a support medium, which comprises steps of:
   (1) detecting at least two bands in the lower part of each resolved row and numbering the bands consecutively from the lower end;
   (2) obtaining correlation between the band's number and a resolved distance thereof for each resolved row;
   (3) determining difference in the resolved distance between the resolved rows from the resulting correlation and making correction for resolved position on each row by taking said difference as locational deviation of the rows from each other; and
   (4) detecting all bands on every resolved row and determining the sequence of the bands on the basis of their positions.

10. The signal processing method as claimed in claim 9, wherein said bands are detected by extracting digital signals along the resolving direction of each resolved row and then finding out positions where level of the extracted signal is maximum, in said steps (1) and (4).

11. The signal processing method as claimed in claim 9, wherein said correlation between the band's number and the resolved distance thereof is obtained as a regression line or a regression curve, in said step (2).

12. The signal processing method as claimed in claim 11, wherein said difference in the resolved distance between the resolved rows is determined as a difference in an intercept of the regression line or the regression curve, in said step (3).

13. The signal processing method as claimed in claim 9, wherein correction for the resolved distance is made on each resolved row by detecting inclination of at least one band to the resolving direction for each row and then determining a relative position of said band on other rows on the basis of the inclination thereof, prior to said step (1).

14. The signal processing method as claimed in claim 9, wherein the mixture of the base-specific DNA fragments consists of the four groups of:
   (1) guanine-specific DNA fragments;
   (2) adenine-specific DNA fragments;
   (3) thymine-specific DNA fragments; and
   (4) cytosine-specific DNA fragments;
and the resolved rows consist of four rows formed by resolving each of said four groups of the base-specific DNA fragments on the support medium.

15. The signal processing method as claimed in claim 9, wherein said digital signals corresponding to the autoradiograph are obtained by placing the support medium and a stimulable phosphor sheet comprising a stimulable phosphor together in layers to record the autoradiograph of the plural resolved rows on the phosphor sheet as an energy-stored image, irradiating said phosphor sheet with stimulating rays and photoelectrically detecting the autoradiograph as stimulated emission.

16. The signal processing method as claimed in claim 9, wherein said digital signals corresponding to the autoradiograph are obtained by placing the support medium and a radiosensitive material together in layers to record the autoradiograph of the plural resolved rows on the radiosensitive material as a visible image and photoelectrically reading out the autoradiograph visualized on said radiosensitive material.

17. A signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in one-dimensional direction on a support medium, which comprises steps of:
   (1) detecting at least two bands in the lower part of each resolved row and numbering the bands consecutively from the lower end;
   (2) obtaining correlation between the band's number and a resolved distance thereof for each resolved row;
   (3) determining difference in the resolved distance between the resolved rows from the resulting correlation;
   (4) detecting at least one band in the more upper part of each resolved row, making correction for resolved position on each band by taking the resulting difference as locational deviation of the rows from each other, and then numbering the bands consecutively on the basis of their positions;
   (5) obtaining the correlation between the band's number and the resolved distance with respect to the previously detected bands plus the band detected in the step (4) for each resolved row; and
   (6) determining the sequence of all bands on every resolved row on the basis of their corrected positions by repeating the steps (3) to (5).

18. The signal processing method as claimed in claim 17, wherein said bands are detected by extracting digital signals along the resolving direction of each resolved row and then finding out positions where level of the extracted signal is maximum, in said steps (1) and (4).

19. The signal processing method as claimed in claim 17, wherein said correlation between the band's number and the resolved distance thereof is obtained as a regression line or a regression curve, in said step (2).

20. The signal processing method as claimed in claim 19, wherein said difference in the resolved distance between the resolved rows is determined as that obtained by extrapolating the regression line or the regression curve in the direction of increasing the band's number, in said step (3).

21. The signal processing method as claimed in claim 17, wherein said correlation between the band's number and the resolved distance is obtained with respect to the previously detected bands plus the band detected in the step (4) and minus the bands having the lower number for each resolved row, in said step (5).

22. The signal processing method as claimed in claim 17, wherein correction for the resolved distance is made on each resolved row by detecting inclination of at least one band to the resolving direction for each row and then determining a relative position of said band on the other rows on the basis of the inclination thereof, prior to said step (1).

23. The signal processing method as claimed in claim 17, wherein the mixture of the base-specific DNA fragments consists of the four groups of:
   (1) guanine-specific DNA fragments;
   (2) adenine-specific DNA fragments;
   (3) thymine-specific DNA fragments; and
   (4) cytosine-specific DNA fragments;
and the resolved rows consist of four rows formed by resolving each of said four groups of the base-specific DNA fragments on the support medium.

24. The signal processing method as claimed in claim 17, wherein said digital signals corresponding to the autoradiograph are obtained by placing the support medium and a stimulable phosphor sheet comprising a stimulable phosphor together in layers to record the autoradiograph of the plural resolved rows on the phosphor sheet as an energy-stored image, irradiating said phosphor sheet with stimulating rays and photoelectrically detecting the autoradiograph as stimulated emission.

25. The signal processing method as claimed in claim 17, wherein said digital signals corresponding to the autoradiograph are obtained by placing the support medium and a radiosensitive material together in layers to record the autoradiograph of the plural resolved rows on the radiosensitive material as a visible image and photoelectrically reading out the autoradiograph visualized on said radiosensitive material.

* * * * *